(12) United States Patent
Burisch et al.

(10) Patent No.: US 9,377,382 B2
(45) Date of Patent: Jun. 28, 2016

(54) METHOD AND APPARATUS FOR DETACHING AND/OR ISOLATING A HISTOLOGICAL SAMPLE

(71) Applicant: Leica Biosystems Nussloch GmbH, Nussloch (DE)

(72) Inventors: Arne Burisch, Braunschweig (DE); Christian Löchte, Braunschweig (DE); Annika Raatz, Braunschweig (DE); Hermann Ulbrich, Bad Schoenborn (DE); Karl-Heinrich Westerhoff, Eppingen (DE)

(73) Assignee: Leica Biosystems Nussloch GmbH, Nussloch (DE)

( * ) Notice: Subject to any disclaimer, the term of this patent is extended or adjusted under 35 U.S.C. 154(b) by 79 days.

(21) Appl. No.: 14/276,542

(22) Filed: May 13, 2014

(65) Prior Publication Data

US 2014/0245842 A1  Sep. 4, 2014

Related U.S. Application Data

(62) Division of application No. 13/451,581, filed on Apr. 20, 2012, now Pat. No. 8,757,016.

(30) Foreign Application Priority Data

Apr. 20, 2011  (DE) .......................... 10 2011 002 195

(51) Int. Cl.
*G01N 1/28* (2006.01)
*G01N 1/36* (2006.01)

(52) U.S. Cl.
CPC ... *G01N 1/28* (2013.01); *G01N 1/36* (2013.01)

(58) Field of Classification Search
None
See application file for complete search history.

(56) References Cited

U.S. PATENT DOCUMENTS

| 3,537,271 | A | * | 11/1970 | Montag | ................. F17C 13/021 137/210 |
| 5,821,115 | A | | 10/1998 | Graupner | |
| 8,357,544 | B2 | * | 1/2013 | Ingenhoven | ............ B01L 3/021 141/2 |
| 2007/0125170 | A1 | * | 6/2007 | Tenney | ................... G01F 23/14 73/290 R |
| 2010/0055788 | A1 | | 3/2010 | Ulbrich et al. | |
| 2011/0087448 | A1 | | 4/2011 | Haberkorn | |

FOREIGN PATENT DOCUMENTS

| DE | 3047414 | 7/1982 |
| DE | 10163488 | 7/2003 |
| DE | 102009022349 | 12/2010 |
| EP | 0077477 | 4/1983 |

(Continued)

*Primary Examiner* — Robert R Raevis
(74) *Attorney, Agent, or Firm* — Hodgson Russ LLP

(57) ABSTRACT

The invention provides a method for detaching and/or isolating a histological sample that is adhering to another sample and/or to the inside of a cassette, for example as a result of solidification of an embedding medium within a cassette. The sample is immobilized in a sample receiving chamber above a first fill level of a liquid that is suitable for counteracting the adhesion; and that the fill level of the liquid is then elevated at least until said level reaches the sample. An apparatus according to the present invention that can be used for carrying out the method comprises a sample receiving chamber and an adjusting chamber, the adjusting chamber being connected to the sample receiving chamber in such a way that a change in the fill level height of the liquid in the sample receiving chamber is producible by changing the pressure existing in the adjusting chamber.

30 Claims, 4 Drawing Sheets

(56) References Cited

FOREIGN PATENT DOCUMENTS

Figure 1:
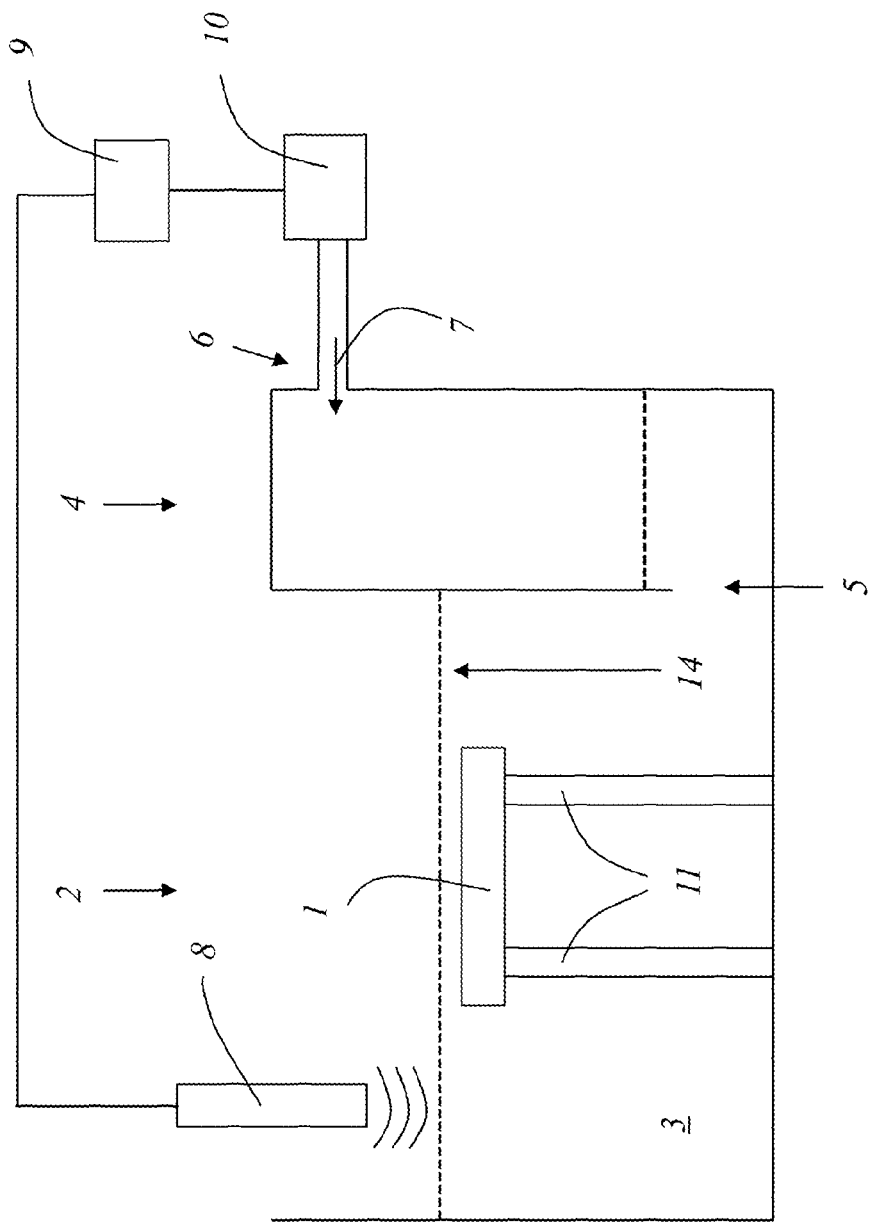

| | | |
|---|---|---|
| EP | 0969277 | 1/2000 |
| GB | 1569459 | 6/1980 |
| GB | 2466868 | 7/2010 |
| WO | 9629866 | 10/1996 |
| WO | 03029845 | 4/2003 |

\* cited by examiner

METHOD AND APPARATUS FOR DETACHING AND/OR ISOLATING A HISTOLOGICAL SAMPLE

CROSS REFERENCE TO RELATED APPLICATIONS

This application claims priority of German patent application number 10 2011 002 195.7 filed Apr. 20, 2011, the entire disclosure of which is incorporated by reference herein.

FIELD OF THE INVENTION

The invention relates to a method for detaching and/or isolating a histological sample that, in particular after an infiltration operation, is adhering to another sample and/or to the inside of a cassette, for example as a result of solidification of the embedding medium.

The invention further relates to an apparatus for treating histological samples, in particular for detaching and/or isolating a histological sample that, in particular after an infiltration operation, is adhering to another sample and/or to the inside of a cassette, having a sample receiving chamber which is embodied and intended to be filled at least partly with a liquid, in particular with liquid paraffin.

BACKGROUND OF THE INVENTION

In the context of the conditioning of histological samples for later microtoming, in particular in the preparation of histological samples in the context of an embedding process, they are firstly fixed by the application of various chemicals. The tissue liquid originally present in the natural cavities of the sample is thereby replaced, in multiple steps, by a fixing liquid, for example by formalin. In order to convert the fixed samples into a state that permits sectioning by means of a microtome, the fixing liquid is replaced by an embedding medium, for example paraffin, gelatin, agar, nitrocellulose, polyester wax, polyethylene glycol, or plastic. During the aforementioned processes, the samples are usually located in a cassette that comprises a plurality of sieve-like openings so that the chemicals can flow around the samples. A particular embodiment of such a cassette is known, for example, from DE 43 33 118 A1.

After infiltration of the embedding medium into the samples, the excess paraffin is drained off. After this step, the samples can be located anywhere within the cassette; because of the paraffin residues adhering to them, the samples as a rule adhere to the cassette cover, in the cassette cavity, and/or to one another.

Before further processing, in particular for automated, machine-controlled further processing, namely casting the samples into a paraffin block (called "blocking"), the samples must be separated and removed from the cassette. In order to allow the samples to be separated from one another and removed from the cassette, the paraffin that causes the aforementioned adhesion must be melted again. For this, the cassette (in the closed state or in the flipped-open state) can be introduced into a paraffin bath. This must occur largely without jolting. In addition, contamination and functional impairment due to solidifying paraffin must be avoided.

DE 10 2008 039 875 A1 discloses a method and an apparatus for infiltrating tissue samples with paraffin. The apparatus comprises a retort that is embodied as a closable chamber and that can be filled, in valve-controlled fashion via conduits, from a reservoir container of paraffin. For this a vacuum is applied to the closed chamber of the retort so that paraffin is conveyed through the conduit and through special distributors and valves into the retort. In particular because the samples, and the cassette in which the samples are arranged, are not accessible during flooding of the retort, an apparatus of this kind is unsuitable as a paraffin bath for detaching or isolating samples adhering to one another, or samples that are adhering in the interior of a cassette.

SUMMARY OF THE INVENTION

It is an object of the present invention to describe a method that permits detachment or isolation, with as little disruption as possible, of a sample located in a cassette.

The object is achieved by a method which is characterized in that the sample is immobilized in a sample receiving chamber above a first fill level of a liquid, in particular liquid paraffin, that is suitable for counteracting the adhesion; and that the fill level of the liquid is then elevated, in particular under open- and/or closed-loop control, at least until said level reaches the sample.

The further object of the present invention is to describe an apparatus that is usable for detachment and/or isolation, with as little disruption as possible, of a histological sample that, in particular after a infiltration operation, is adhering to another sample and/or to the inside of a cassette.

The object is achieved by an apparatus of the kind cited above which is characterized in that an adjusting chamber is provided which is connected to the sample receiving chamber in such a way that a change in the fill level height of the liquid in the sample receiving chamber is producible by changing the pressure existing in the adjusting chamber.

The method according to the present invention has the very particular advantage that a sample can be detached, for example from the cassette cover or from another sample, by targeted setting of the fill level. Advantageously and in accordance with the present invention, the cassette is not, in this context, moved into the liquid paraffin. Instead the cassette together with the samples located therein, which has been conveyed into the sample receiving chamber, remains at rest, for example in a holder, while the liquid is brought to the cassette and to the samples by raising the liquid level. Unintentional jolting of the cassette and the samples is, in particular, thereby effectively avoided.

In order to detach a sample from the cassette cover, the liquid level can, according to the present invention, firstly be raised until the cassette is completely flooded. The liquid level can then be lowered. The fill level of the liquid can advantageously be set and/or established, in particular after lifting of the cassette cover, so that exclusively the underside of the sample or undersides of the samples is/are wetted with the liquid, so that they cannot adhere to the cassette bottom. With this setting, individual samples can easily be separated from one another inside the cassette, for example using a tweezers, or be removed from the cassette with a gripper.

The apparatus according to the present invention has the very particular advantage that the fill level height can be set largely arbitrarily and with very high accuracy. In addition, the apparatus according to the present invention has the advantage that contamination, clogging, or sticking of valves or conduits for the liquid is effectively avoided. The apparatus according to the present invention can instead be embodied so that neither valves nor conduits that come into contact with the liquid (in particular, with paraffin) are necessary.

The aforesaid advantages make the apparatus according to the present invention ideal for automatic, machine-controlled treatment of histological samples, especially in the context of a fully automatic embedding process, since the apparatus according to the present invention can be embodied in largely maintenance-free or at least extremely low-maintenance fashion.

In a particular embodiment of the apparatus according to the present invention, provision is made that as a consequence of a change in the pressure existing in the adjustment chamber, liquid flows out of one of the chambers into the other chamber. Provision can be made in particular that upon a reduction in the pressure existing in the adjusting chamber, liquid flows out of the sample receiving chamber into the adjusting chamber. Alternatively or additionally, provision can also be made that upon an elevation of the pressure existing in the adjusting chamber, liquid flows out of the adjusting chamber into the sample chamber.

According to the present invention, the apparatus can be embodied in such a way that the fill level height is arranged below the cassette and/or below a receptacle for the cassette when atmospheric pressure exists in the adjusting chamber. By raising the pressure in the adjusting chamber, for example by forcing in air, the fill level height can be raised largely arbitrarily, in particular above the upper edge of the cassette. An embodiment of this kind has the advantage that a vacuum does not need to be generated. A decrease in the fill level height is effected by lowering the pressure in the adjusting chamber again, for example by releasing air. Analogously, it is also possible according to the present invention to embody the apparatus in such a way that it requires only negative pressure. Provision can also be made according to the present invention that in order to raise the fill level height, the pressure in the adjusting chamber is elevated, for example by forcing a fluid into the adjusting chamber, whereas a lowering of the fill level height is accomplished by generating a negative pressure, for example by aspirating a fluid out of the adjusting chamber.

As already mentioned, a change in the pressure in the adjusting chamber can be accomplished by forcing in and/or aspirating a fluid and/or allowing it to flow out. The fluid can be, for example, a gas or a gas mixture. The fluid can, however, also be a liquid, preferably one differing from the liquid that is to be brought into contact with the histological sample. The fluid can be, for example, a liquid that does not mix with the liquid that is to be brought into contact with the sample, and that preferably has a lower density than the liquid that is to be brought into contact with the samples being treated.

In a particular embodiment, the pressure existing in the adjusting chamber is settable by modifying the volume of the adjusting chamber. For example, the adjusting chamber can comprise a displaceable plunger that is arranged displaceably, in fluid-tight fashion, inside a cylindrical part of the adjusting chamber.

In a very particularly advantageous embodiment, the adjusting chamber is embodied annularly and/or in frame-shaped fashion. An embodiment of this kind has the very particular advantage that the sample receiving chamber can be at least partly surrounded by the adjusting chamber. With such an embodiment, the liquid flows homogeneously from all sides into the sample receiving chamber upon an elevation of the fill level, and out of the sample receiving chamber upon a lowering of the fill level, so that the generation of disruptive waves inside the sample receiving chamber is largely avoided.

In an embodiment of the apparatus according to the present invention that is particularly compact and of particularly robust construction, the adjusting chamber and the sample receiving chamber are arranged inside a shared pan. Provision can be made in particular for the adjusting chamber to be constituted at least partly from a turned-over rim of a pan.

In order to avoid unnecessary conduits for the liquid to be brought into contact with the samples, provision can advantageously be made that the sample receiving chamber and the adjusting chamber are arranged at least in part directly adjacent to one another. It is also possible, however, for the sample receiving chamber and the adjusting chamber to be made up of respectively separate contains that are interconnected via a conduit. With an embodiment of this kind as well, at least one valve that comes into contact with the liquid is unnecessary.

In a advantageous embodiment of the apparatus, a heating apparatus is provided for heating the liquid located in the adjusting chamber and/or in the sample receiving chamber. The heating apparatus can be embodied, for example, as a heating film. The heating apparatus, for example in the form of a heating film, can in particular be arranged effectively and in protected fashion under the sample receiving chamber and/or under the adjusting chamber.

In an advantageous embodiment of the apparatus according to the present invention, the sample receiving chamber is embodied in such a way that the samples and/or the cassette located therein is accessible, in particular from above. The sample chamber according to the present invention can in this regard advantageously be embodied and arranged, in particular, in such a way that atmospheric pressure and/or ambient pressure acts on the surface of the liquid located in the sample receiving chamber.

In an advantageous embodiment, a fill level sensor is provided. It is particularly advantageous to use a fill level sensor that operates in non-contact fashion, in particular with respect to the liquid. For example, the fill level sensor can be embodied as an ultrasonic sensor. The fill level sensor is preferably embodied and arranged so as to enable a maximally exact determination of the sample receiving chamber fill level of the liquid.

The apparatus according to the present invention can advantageously comprise an open-loop fill level control system or closed-loop fill level control system. Provision can be made in this context, for example, that the pressure existing in the adjusting chamber is directly or indirectly set as a function of signals of a fill level sensor. An open- or closed-loop fill level control system of this kind can advantageously be implemented on the basis of stored-program electronic modules.

In an advantageous embodiment, a mount for direct and/or indirect, preferably releasable, immobilization of at least one sample and/or one cassette is provided in the sample receiving chamber. Provision can be made in particular that the mount comprises a clip mount and/or a bayonet mount for one or more cassettes. Provision can also be made that the mount comprises a first receptacle for a cassette and a further receptacle for the cover of the cassette. Provision can be made in this context in particular that the bottom of the cassette located in the first receptacle, and the turned-around cover located in the further receptacle, are located in the same horizontal plane.

Further goals, advantages, features, and possible applications of the present invention are evident from the description below of an exemplifying embodiment with reference to the drawings. In this context, all features described and/or graphically depicted, independently or in any useful combination, constitute the subject matter of the present invention, irrespective of their grouping in the claims or their internal references.

BRIEF DESCRIPTION OF THE DRAWINGS VIEWS

Figure 2:
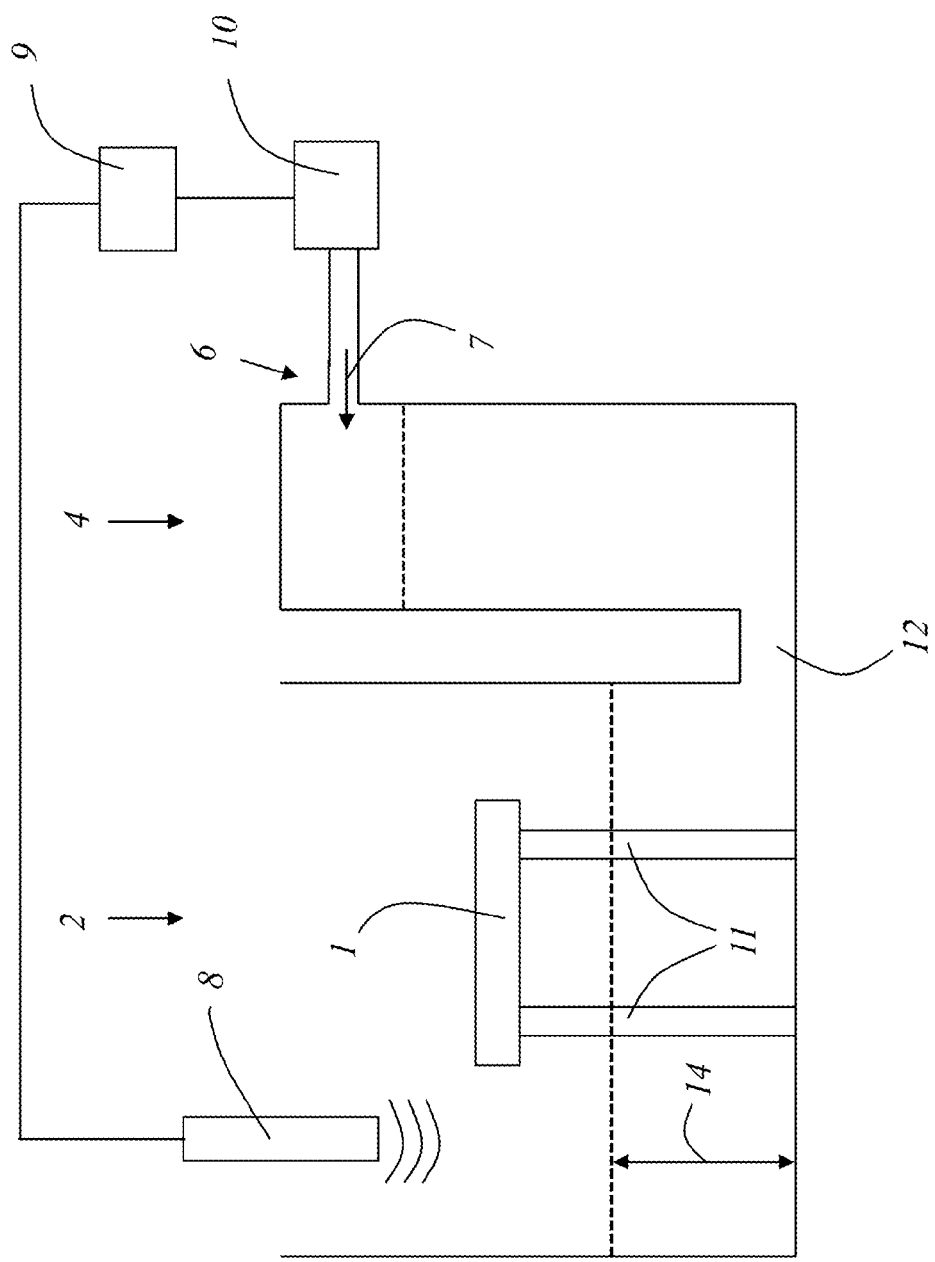
Figure 3:
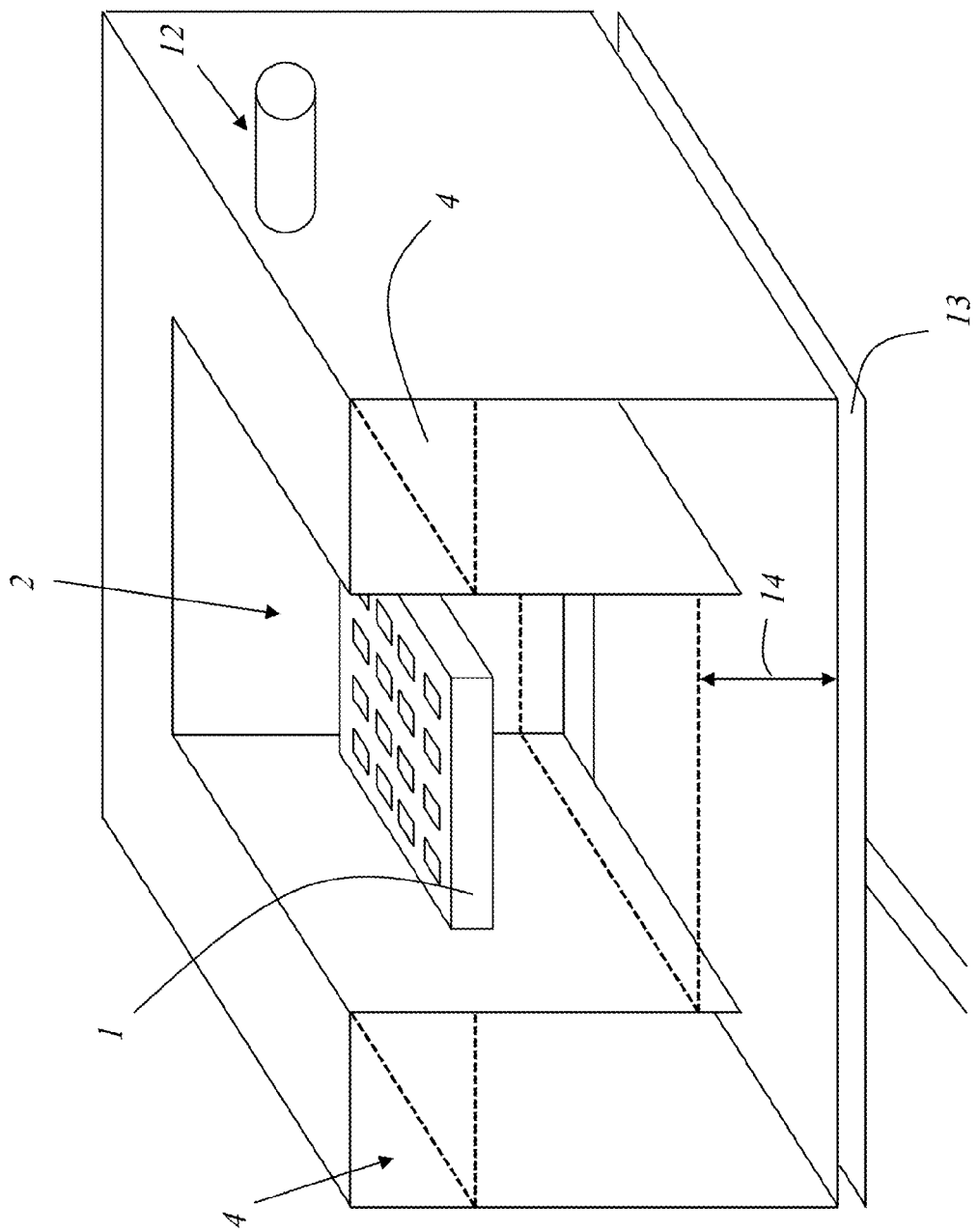
Figure 4:
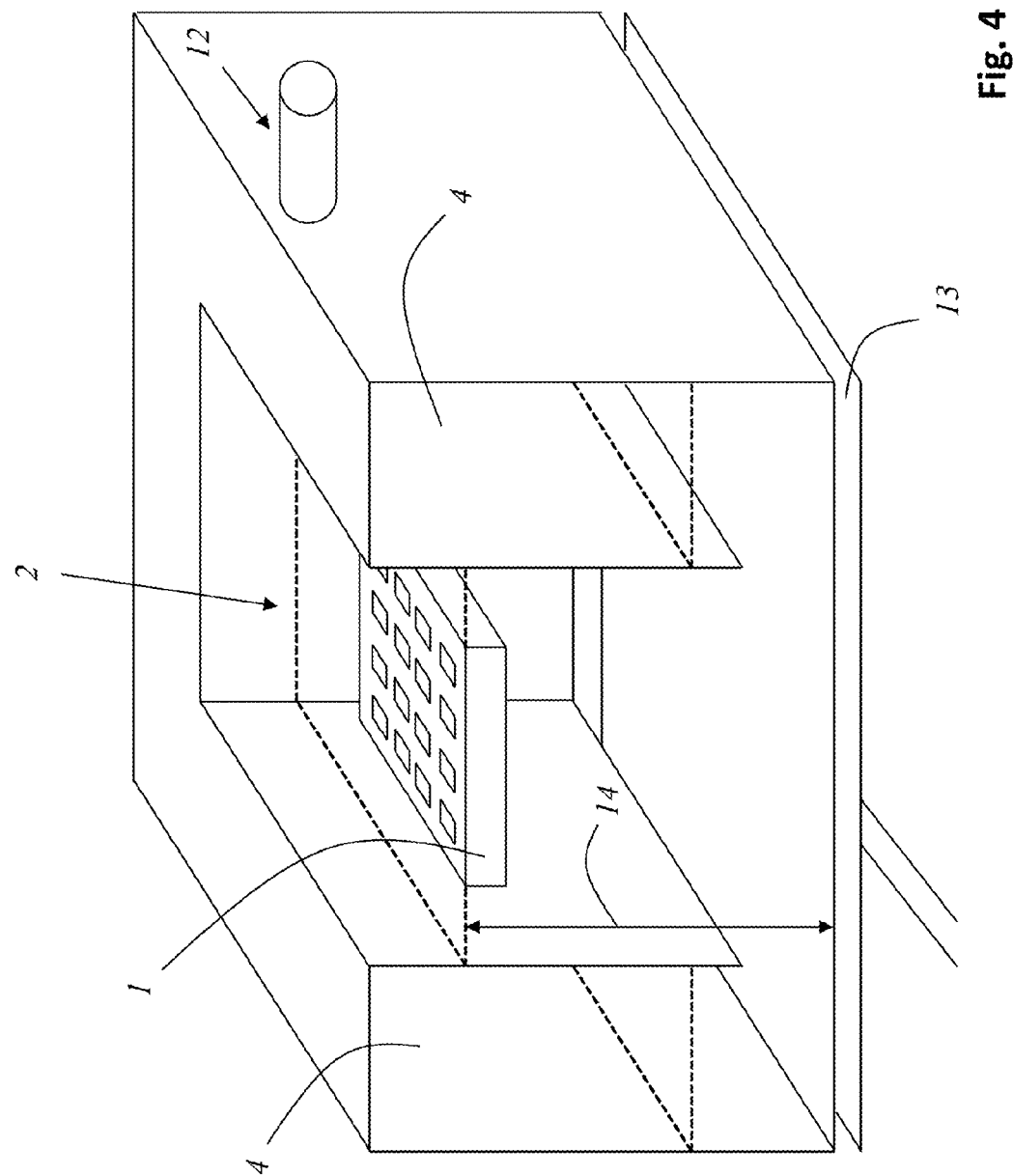

In the drawings:

FIG. 1 schematically depicts an apparatus according to the present invention;

FIG. 2 schematically depicts another apparatus according to the present invention;

FIG. 3 is a perspective depiction of a further apparatus according to the present invention with a lowered fill level height, in a perspective depiction; and FIG. 4 shows the further apparatus according to the present invention with a raised fill level height.

DETAILED DESCRIPTION OF THE INVENTION

FIG. 1 is a schematic depiction of an apparatus according to the present invention for treating histological samples that are arranged in a cassette 1. The apparatus comprises a sample receiving chamber 2 that is embodied and intended to be filled at least partly with a liquid 3, in particular with liquid paraffin. The apparatus furthermore comprises an adjusting chamber 4 that is connected via a passthrough 5 to sample receiving chamber 2 in such a way that a change in the fill level height of liquid 3 of the sample receiving chamber can be brought about by changing the pressure existing in adjusting chamber 4.

An elevation of the pressure existing in adjusting chamber 4 is brought about by forcing compressed air through a compressed-air connector 6 of adjusting chamber 4, as illustrated by arrow 7. The compressed air forced into adjusting chamber 4 displaces liquid 3 located in adjusting chamber 4 so that said liquid flows through passthrough 5 into sample receiving chamber 2, with the result that the fill level height of the liquid in sample receiving chamber 2 rises.

The apparatus comprises a fill level sensor 8, embodied as an ultrasonic sensor, that enables the fill level height to be sensed in non-contact fashion. The signals of fill level sensor 8 are forwarded to a fill level height control system 9 that, as a function of the signals of fill level sensor 8, sets the pressure existing in the adjusting chamber by means of a compressed-air valve 10, in such a way that a fill level height preselected by the user is reached, and is maintained by closed-loop control, in the sample receiving chamber.

Cassette 1 is immobilized releasably on a mount 11 by means of bayonet fasteners (not depicted).

FIG. 2 shows another apparatus according to the present invention that differs from the apparatus depicted in FIG. 1 in that the sample receiving chamber and the adjusting chamber are not arranged directly adjacent to one another, but instead the sample receiving chamber and adjusting chamber each comprise separate containers that are interconnected via a conduit 12 for the liquid.

FIG. 3 is a perspective cross-sectional depiction showing a further apparatus according to the present invention, having a sample receiving chamber 2 that is surrounded in frame-like fashion by a peripheral adjusting chamber, with a lowered fill level height. The adjusting chamber comprises a connector piece 12 for forcing in and aspirating a fluid. Adjusting chamber 4 and sample receiving chamber 2 are arranged de facto in a shared pan, the adjusting chamber being constituted substantially from a turned-over rim of the pan. A heating film 13 is arranged below sample receiving chamber 2 and adjusting chamber 4. The liquid located in the adjusting chamber and in the sample receiving chamber can be heated with the aid of the heating film.

Located in the sample receiving chamber is a cassette 1 that can be flooded by forcing a fluid into the adjusting chamber, as depicted in FIG. 4. As in the case of the apparatuses depicted in FIGS. 1 and 2, forcing a fluid into adjusting chamber 4 causes liquid to be displaced out of adjusting chamber 4, so that fill level 14 in the sample receiving chamber rises.

The respective surfaces of the liquid in adjusting chamber 4 and in sample receiving chamber 2 are depicted in the Figures with dashed lines.

PARTS LIST

1 Cassette
2 Sample receiving chamber
3 Liquid
4 Adjusting chamber
5 Passthrough
6 Compressed-air connector
7 Compressed air
8 Fill level sensor
9 Fill level control system
10 Compressed-air valve
11 Mount
12 Conduit
13 Heating film
14 Fill level in sample receiving chamber 2

What is claimed is:

1. An apparatus for treating histological samples that are adhering to another sample and/or to the inside of a cassette (1), the apparatus comprising:
   a sample receiving chamber (2) which is embodied and intended to be filled at least partly with a liquid (3),
   an adjusting chamber (4) connected to the sample receiving chamber (2) such that a change in the fill level of the liquid (3) in the sample receiving chamber (2) is producible by changing the pressure existing in the adjusting chamber (4), and
   a mount (11) in the sample receiving chamber (2) for immobilization of a cassette.

2. The apparatus according to claim 1, wherein as a consequence of an increase of pressure in the adjusting chamber (4), liquid (3) flows out of the adjusting chamber and into the sample receiving chamber (2), and as a consequence of a decrease of pressure in the adjusting chamber (4), liquid (3) flows out of the sample receiving chamber and into the adjusting chamber (4).

3. The apparatus according to claim 2, wherein the sample receiving chamber (2) is configured and arranged such that ambient atmospheric pressure acts on the surface of the liquid (3) located in the sample receiving chamber (2).

4. The apparatus according to claim 1, wherein the pressure existing in the adjusting chamber (4) is settable.

5. The apparatus according to claim 1, wherein the pressure existing in the adjusting chamber (4) is settable by introducing a fluid into the adjusting chamber (4) and by releasing or aspirating a fluid out of the adjusting chamber (4).

6. The apparatus according to claim 1, wherein the adjusting chamber is modifiable in volume to set the pressure existing in the adjusting chamber (4).

7. The apparatus according to claim 1, wherein the adjusting chamber (4) is annularly shaped.

8. The apparatus according to claim 1, wherein the adjusting chamber (4) is has a shape of a rectangular frame.

9. The apparatus according to claim 1, wherein the sample receiving chamber (2) is at least partly surrounded by the adjusting chamber (4).

10. The apparatus according to claim 1, wherein the adjusting chamber (4) and the sample receiving chamber (2) are arranged directly adjacent to one another.

11. The apparatus according to claim 1, further comprising a pan, wherein the adjusting chamber (4) and the sample receiving chamber (2) are arranged inside the pan.

12. The apparatus according to claim 1, wherein the adjusting chamber (4) is constituted at least partly from a turned-over rim of a pan.

13. The apparatus according to claim 1, further comprising a heating apparatus arranged for heating the liquid (3) located in the adjusting chamber (4) and in the sample receiving chamber (2).

14. The apparatus according to claim 13, wherein the heating apparatus includes a heating film (13) below the adjusting chamber (4) and the sample receiving chamber (2).

15. The apparatus according to claim 1, further comprising a fill level sensor (8) for determining a fill level of the liquid (3) in the sample receiving chamber (2).

16. The apparatus according to claim 15, wherein the fill level sensor (8) operates without contacting the liquid (3).

17. The apparatus according to claim 16, wherein the fill level sensor (8) is an ultrasonic sensor.

18. The apparatus according to claim 15, further comprising an open-loop or closed-loop fill level control system (9) for controlling the fill level of liquid in the sample receiving chamber (2).

19. The apparatus according to claim 18, wherein the control system (9) is a closed-loop control system which directly or indirectly sets the pressure existing in the adjusting chamber (4) as a function of signals from the fill level sensor (8).

20. An apparatus for treating histological samples that are adhering to another sample and/or to the inside of a cassette (1), the apparatus comprising:
a sample receiving chamber (2) which is embodied and intended to be filled at least partly with a liquid (3),
an adjusting chamber (4) connected to the sample receiving chamber (2) such that a change in the fill level of the liquid (3) in the sample receiving chamber (2) is producible by changing the pressure existing in the adjusting chamber (4), and
a mount (11) in the sample receiving chamber (2) for immobilization of at least one sample.

21. The apparatus according to claim 20, wherein as a consequence of an increase of pressure in the adjusting chamber (4), liquid (3) flows out of the adjusting chamber and into the sample receiving chamber (2), and as a consequence of a decrease of pressure in the adjusting chamber (4), liquid (3) flows out of the sample receiving chamber and into the adjusting chamber (4).

22. The apparatus according to claim 21, wherein the sample receiving chamber (2) is configured and arranged such that ambient atmospheric pressure acts on the surface of the liquid (3) located in the sample receiving chamber (2).

23. The apparatus according to claim 20, wherein the pressure existing in the adjusting chamber (4) is settable.

24. The apparatus according to claim 20, wherein the pressure existing in the adjusting chamber (4) is settable by introducing a fluid into the adjusting chamber (4) and by releasing or aspirating a fluid out of the adjusting chamber (4).

25. The apparatus according to claim 20, wherein the adjusting chamber is modifiable in volume to set the pressure existing in the adjusting chamber (4).

26. The apparatus according to claim 20, further comprising a fill level sensor (8) for determining a fill level of the liquid (3) in the sample receiving chamber (2).

27. The apparatus according to claim 26, wherein the fill level sensor (8) operates without contacting the liquid (3).

28. The apparatus according to claim 27, wherein the fill level sensor (8) is an ultrasonic sensor.

29. The apparatus according to claim 26, further comprising an open-loop or closed-loop fill level control system (9) for controlling the fill level of liquid in the sample receiving chamber (2).

30. The apparatus according to claim 29, wherein the control system (9) is a closed-loop control system which directly or indirectly sets the pressure existing in the adjusting chamber (4) as a function of signals from the fill level sensor (8).

* * * * *